(12) United States Patent
Brieden et al.

(10) Patent No.: US 6,433,170 B1
(45) Date of Patent: Aug. 13, 2002

(54) METHOD FOR PRODUCING 4-[2',5'-DIAMINO-6'-HALOPYRIMIDINE-4'-YL) AMINO]- CYCLOPENT-2-ENYLMETHANOLS

(75) Inventors: Walter Brieden, Brig-Glis (CH); Elie Saikali, Cedars, PA (US)

(73) Assignee: Lonza Group (CH)

( * ) Notice: Subject to any disclaimer, the term of this patent is extended or adjusted under 35 U.S.C. 154(b) by 0 days.

(21) Appl. No.: 09/807,976

(22) PCT Filed: Oct. 29, 1999

(86) PCT No.: PCT/EP99/08270

§ 371 (c)(1),
(2), (4) Date: Jun. 18, 2001

(87) PCT Pub. No.: WO00/26193

PCT Pub. Date: May 11, 2000

Related U.S. Application Data

(60) Provisional application No. 60/146,105, filed on Jul. 29, 1999.

(30) Foreign Application Priority Data

Oct. 30, 1998 (EP) .............................. 98120529

(51) Int. Cl.[7] ............................................ C07D 239/50
(52) U.S. Cl. ..................................................... 544/323
(58) Field of Search ........................................ 544/323

(56) References Cited

U.S. PATENT DOCUMENTS

| | | | |
|---|---|---|---|
| 4,916,224 A | 4/1990 | Vince et al. | 544/276 |
| 4,931,559 A | 6/1990 | Vince et al. | 554/276 |
| 4,950,758 A | 8/1990 | Vince et al. | 544/276 |
| 5,175,292 A | 12/1992 | Vince et al. | 544/323 |
| 5,206,435 A | 4/1993 | Daluge | 564/1 |
| 5,216,161 A | 6/1993 | Hanson | 544/330 |
| 5,567,703 A | 10/1996 | Vince et al. | 514/261 |
| 5,583,226 A | 12/1996 | Stucky et al. | 544/322 |
| 5,631,370 A | 5/1997 | Vince et al. | 544/244 |
| 5,663,340 A | 9/1997 | Stucky et al. | 544/330 |
| 5,693,800 A | 12/1997 | Stucky et al. | 544/322 |
| 5,744,601 A | 4/1998 | Stucky et al. | 544/330 |
| 5,763,607 A | 6/1998 | Vince et al. | 544/277 |
| 5,962,684 A | 10/1999 | Vince et al. | 544/254 |

FOREIGN PATENT DOCUMENTS

| | | |
|---|---|---|
| DE | 3901 502 A1 | 7/1989 |
| EP | 0 684 236 A2 | 4/1995 |
| EP | 0 434 450 A2 | 12/1999 |
| WO | WO 91/01310 | 2/1991 |
| WO | WO 97/45529 | 12/1997 |
| WO | PCT/EP99/08270 | 5/2000 |

OTHER PUBLICATIONS

Legraverend, M., et al., Synthesis, No. 7, (1990), pp. 587–589.

Andersen, M.W., et al., Tetrahedron Letters, vol. 37, No. 45, (1996), pp. 8147–8150.

Vince et al., Journal of Medicinal Chemistry, US, American Chemical Society, vol. 33, No. 1, (1990), pp. 17 to 21.

Evans, C.T., et al., Journal of The Chemical Society, Perkins Transaction 1, GB, Chemical Society, No. 5, (1992), pp. 589–592.

*Primary Examiner*—John M. Ford
(74) *Attorney, Agent, or Firm*—Fisher, Christen & Sabol

(57) ABSTRACT

The invention relates to a novel method for producing 4-[(2',5'-diamino-6'-halopyrimidine-4'-yl)amino]- cyclopent-2-enylmethanols of general formula (I), wherein X represents a halogen atom. According to the inventive method amino-4,6-halopyrimidine of general formula (II), wherein X has the aforementioned meaning, is reacted with a 4-aminocyclopent-2-enylmethanol of formula (III) or with a salt thereof in the presence of a base in a polar protic solvent.

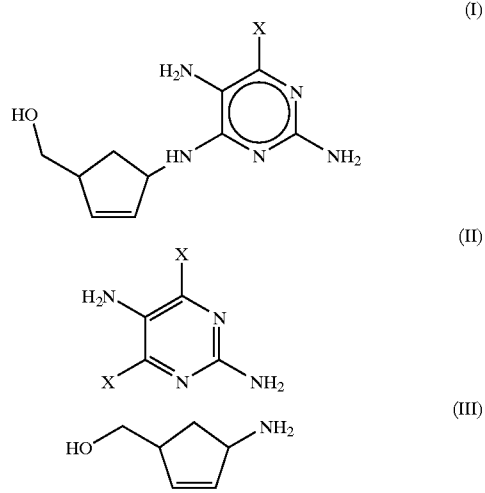

16 Claims, No Drawings

METHOD FOR PRODUCING 4-[2',5'-DIAMINO-6'-HALOPYRIMIDINE-4'-YL) AMINO]- CYCLOPENT-2-ENYLMETHANOLS

This application is a 371 national stage application of International Patent Application PCT/EP99/08270, filed on Oct. 29, 1999, which has priority benefit of European Application 98120529.7, filed on Oct. 30,1998, and of U.S. Provisional Application No. 60/146,105, filed on Jul. 29, 1999, which has priority benefit of European Application 98120529.7, filed on Oct. 30,1998.

DESCRIPTION

The present invention relates to a novel process for preparing 4-[(2',5'-diamino-6'-halopyrimidin-4'-yl)amino] cyclopent-2-enylmethanols of the general formula

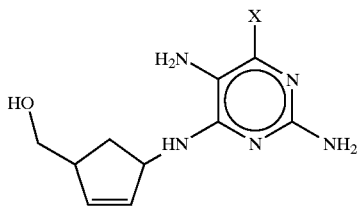

4-[(2',5'-diamino-6'-halopyrimidin-4'-yl)amino] cyclopent-2-enylmethanols are important intermediates for preparing antiviral nucleotide derivatives (WO 91/01310).

The 3-step synthesis of 4-[(2',5'-diamino-6'-chloropyrimidin-4'-yl)-amino]cyclopent-2-enylmethanol starting from 4-acetamidocyclopent-2-enylmethanol by reaction with 2-amino-4,6-dichloropyrimidine in butanol using diisopropylethylamine as base is known. Here, the [(2'-amino-6'-chloro-pyrimidin-4'-yl)amino]cyclopent-2-enylmethanol is initially formed, which is then converted in a subsequent step by diazotization into the corresponding amine which is then hydrolyzed to give the end product (J. Chem. Soc. Perkin Trans, 1, 1992).

This process has the disadvantage that it is too costly and that the desired end product is obtained in only moderate yield.

It is the object of the present invention to provide a 1-step and thus more cost-efficient process for preparing 4-[(2',5'-diamino-6'-halopyrimidin-4'-yl) amino]cyclopent-2-enylmethanols in which the desired products are obtained in good yield.

This object is achieved with the process according to claim 1.

Surprisingly, it has been found that, if instead of 2-amino-4,6-dichloropyrimidine, a 2,5-diamino-4,6-dihalopyrimidine of the general formula

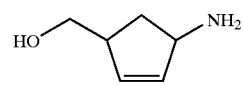

is used as starting material, and this is allowed to react in the presence of a base in a polar protic solvent with a 4-aminocyclopent-2-enylmethanol of the formula

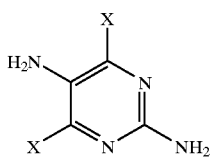

or one of its salts, the desired end product of the general formula

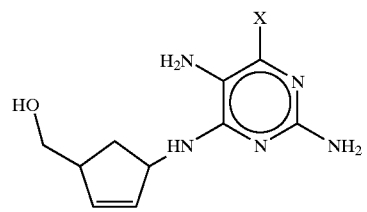

is obtained much more cost-efficiently and in good yield.

The substituent X is a halogen atom, such as F, Cl, Br or I.

The 2,5-diamino-4,6-dihalopyrimidines, such as the 2,5-diamino-4,6-dichloropyrimidine, can be prepared in accordance with EP-A 0 684 326.

The 4-aminocyclopent-2-enylmethanols used can be both the racemic and the optically active compounds, such as (1R, 4S)-, (1S, 4R)-, (1R, 4R)-, or (1S, 4S)-4-amino-cyclopent-2-enylmethanols. Suitable salts thereof are the acid addition salts, in particular, the hydrohalide salts, for example, the hydrochlorides or hydrobromides. These 4-aminocyclopent-2-enylmethanols, in particular, the (1R, 4S)- or the (1S, 4R)-enantiomers, can be prepared in accordance with WO 97/45529.

The reaction is advantageously carried out in the presence of an alkali metal carbonate or alkaline earth metal carbonate, alkali metal bicarbonate or alkaline earth metal bicarbonate or in the presence of nitrogen bases, such as, for example, tert. amines, as the base. The alkali metal carbonate or alkali metal bicarbonate used can be sodium carbonate, potassium carbonate or sodium bicarbonate or potassium bicarbonate. The alkaline earth metal carbonate or alkaline earth metal bicarbonate used can be calcium carbonate or magnesium carbonate or calcium bicarbonate.

Suitable tertiary amines are, for example, triethylamine and diisopropylethylamine. The reaction is preferably carried out in the presence of an alkali metal bicarbonate, such as, sodium bicarbonate, or in the presence of a tertiary amine, such as, diisopropylethylamine.

The base is advantageously employed in excess, based on the 2,5-diamino4,6-dihalopyrimidine; preferably, 1 to 4 mol of base are employed per mol of 2,5-diamino-4,6-dihalopyrimidine.

Suitable polar protic solvents are, in particular, $C_{1-4}$-alcohols, such as methanol, ethanol, propanol and its isomers, and butanol and its isomers.

The reaction is advantageously carried out at a temperature of from 20° C. to the reflux temperature of the solvent in question, preferably from 50° C. to the reflux temperature. Advantageously, the 4-amino-cyclopent-2-enylmethanol and the 2,5-diamino-4,6-dihalopyrimidine are employed in equimolar amounts.

After a customary reaction time of from 2 to 20 h, the end products of formula I, preferably the (1S,4R)-4-[(2',5'-diamino-6'-halopyrimidin-4'-yl)-amino]cyclopent-2-enylmethanol, can then be obtained by customary work-up methods.

EXAMPLES

Example 1

Preparation of 4-[(2',5'-diamino-6'-chloropyrimidin-4'-yl) amino]cyclopent-2-enylmethanol in the Presence of Sodium Bicarbonate.

(1S,4R)-4-aminocyclopent-2-enylmethanol hydrochloride (0.14 mol, 23.25 g), ethanol (3 mol, 138.12 g, 176 ml), 2,5-diamino-4,6-dichloropyrimidine (0.14 mol, 25 g) and sodium bicarbonate (0.34 mol, 28.68 g) were added to a dry reactor. This mixture was heated at reflux temperature (about 80° C.) for 16 h. The rate of conversion was tested by TLC using 13/1 methylene chloride: methanol as the mobile phase. The reaction mixture was cooled to room temperature and stirred for 45 min. The salts were removed by filtration and the filter cake was washed twice with ethanol (0.86 mol, 39.5 g, 50 ml).

⅔ of the organic phase was removed by distillation under reduced pressure, and hexane (150 ml) was then added dropwise. The suspension was cooled to below 10° C. After filtration, the product was dried under reduced pressure at 50° C. This gave 21.5 g (0.08 mol) of end product, corresponding to a yield of 60 percent.

Example 2

Preparation of 4-[(2',5'-diamino-6'-chloropyrimidin-4'-yl) amino]cyclopent-2-Enylmethanol in the Presence of Diisopropylethylamine.

(1S,4R)-4-aminocyclopent-2-enylmethanol hydrochloride (0.14 mol, 23.18 g), butanol (1.26 mol, 93.39 g, 115.3 ml), 2,5-diamino-4,6-dichloropyrimidine (0.14 mol, 25.67 g) and diisopropylethylamine (0.29 mol, 37.09 g, 49.99 ml) were added to a dry reactor. This mixture was heated at reflux temperature (about 115° C.) overnight. The rate of conversion was tested by TLC using 13/1 methylene chloride: methanol as the mobile phase. The reaction mixture was cooled to room temperature. Water was then added, and the mixture was subsequently extracted twice with ethyl acetate.

The organic phase was washed twice with water, and then filtered through celite. ⅔ of the organic phase was removed by distillation under reduced pressure, and hexane was then added dropwise. The suspension was cooled to below 10° C. After filtration, the product was dried Linder reduced pressure at 50° C.

This gave 21.47 g (0.08 mol) of end product, corresponding to a yield of 60 percent.

What is claimed is:

1. Process for preparing 4-[(2',5'-diamino-6'-halopyrimidin-4'-yl)amino]cyclopent-2-enylmethanols of the general formula

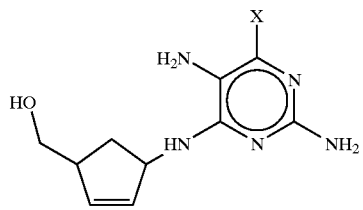

I in which X is a halogen atom, characterized in that a 2,5-diamino-4,6-dihalopyrimidine of the general formula

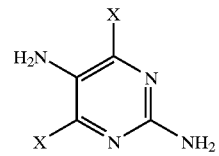

II in which X is defined as above, is reacted with 4-aminocyclopent-2-enylmethanol of the formula

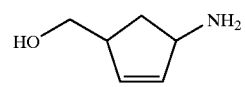

III or one of its salts, in the presence of a base in a polar protic solvent to give the end product of the general formula I.

2. The process according to claim 1, wherein the base used is an alkali metal bicarbonate, an alkaline earth metal bicarbonate, an alkali metal carbonate or an alkaline earth metal carbonate.

3. The process according to claim 2, wherein the polar protic solvent used is a $C_{1-4}$-alcohol.

4. The process according to claim 3, wherein the reaction is carried out at a temperature of from 20° C. to the reflux temperature of the solvent in question.

5. The process according to claim 1, wherein the polar protic solvent is a $C_{1-4}$-alcohol.

6. The process according to claim 1, wherein the reaction is carried out at a temperature of from 20° C. to reflux temperature of the polar protic solvent.

7. A process for preparing a 4-[(2',5'-diamino-6'-halopyrimidin-4'yl)amino]cyclopent-2-enylmethanol of the formula:

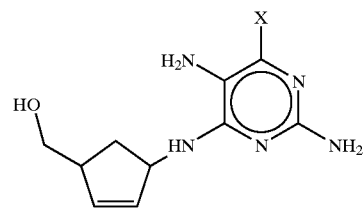

I in which X is halogen, comprising reacting a 2,5-diamino-4,6-dihalopyrimidine of the formula:

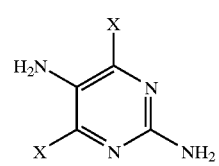

II in which X is defined as above, with a 4-aminocyclopent-2-enylmethanol of the formula:

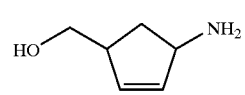

III or one of its salts, in the presence of an alkali metal bicarbonate, an alkaline earth metal bicarbonate, an alkali metal carbonate, an alkaline earth metal carbonate, or a tertiary amine, in a polar protic solvent to provide an end product of the formula I.

8. The process according to claim 7, wherein the polar protic solvent is a $C_{1-4}$-alcohol.

9. The process according to claim 8, wherein the reaction is carried out at a temperature of from 20° C. to the reflux temperature of the polar protic solvent.

10. The process according to claim 7, wherein the reaction is carried out at a temperature of from 20° C. to the reflux temperature of the polar protic solvent.

11. The process according to claim 7, wherein the polar protic solvent used is a $C_{1-4}$-alcohol.

12. The process according to claim 11, wherein the reaction is carried out at a temperature of from 20° C. to the reflux temperature of the solvent in question.

13. The process according to claim 12, wherein the polar protic solvent is a $C_{1-4}$-alcohol.

14. The process according to claim 7, wherein the reaction is carried out at a temperature of from 20° C. to reflux temperature of the polar protic solvent.

15. The process according to claim 7, wherein the base is sodium carbonate, potassium carbonate, sodium bicarbonate, potassium bicarbonate, calcium carbonate, magnesium carbonate, calcium bicarbonate, triethylamine or diisopropylethylamine, and 1 to 4 mols of the base is used per mol of the 2,5-diamino4,6-dihalopyridine.

16. The process according to claim 7, wherein the salt of the compound of formula III is an acid addition salt of the compound of formula III.

* * * * *